United States Patent [19]

Lübbers

[11] 4,008,264

[45] Feb. 15, 1977

[54] PROCESS FOR THE PREPARATION OF AROMATIC THIOCARBOXYLIC ACID AMIDES

[75] Inventor: Henning Lübbers, Schwalbach, Taunus, Germany

[73] Assignee: Hoechst Aktiengesellschaft, Frankfurt am Main, Germany

[22] Filed: May 23, 1975

[21] Appl. No.: 580,484

[30] Foreign Application Priority Data

May 25, 1974 Germany .......................... 2425414
Dec. 10, 1974 Germany .......................... 2458282

[52] U.S. Cl. .............................. 260/470; 260/516; 260/551 S
[51] Int. Cl.[2] ............ C07C 149/40; C07C 153/063; C07C 153/067
[58] Field of Search ............... 260/551 S, 567, 470, 260/516

[56] References Cited

UNITED STATES PATENTS

| | | | |
|---|---|---|---|
| 2,410,862 | 11/1946 | Bousquet et al. | 260/551 S X |
| 3,180,891 | 4/1965 | Ellzey et al. | 260/551 S X |
| 3,715,395 | 2/1973 | Mrozik et al. | 260/551 S |

OTHER PUBLICATIONS

Theilheimer, ed., Synthetic Methods of Organic Chemistry, vol. 24, No. 676 (p. 295), 1970.
Theilheimer, ed., Synthetic Methods of Organic Chemistry, vol. 20, No. 505 (p. 420), 1966.
Buckley et al., CA 40: 1789[3] (1946).
Tsoi et al., CA 57: 16458g (1962).

Primary Examiner—Daniel E. Wyman
Assistant Examiner—Thomas A. Waltz
Attorney, Agent, or Firm—Curtis, Morris & Safford

[57] ABSTRACT

Aromatic thiocarboxylic acid amides are prepared by reaction of aromatic hydrocarbons with hydrogen thiocyanate or a salt of thiocyanic acid in at least 90% hydrofluoric acid. The reaction can be carried out in one single operation without the use of a Lewis acid or another catalyst. The thiocarboxylic acid amides obtained are known from the literature and serve as preliminary products for the preparation of nitriles, amides, carboxylic acids, heterocyclic compounds and the manufacture of plant protecting agents and pharmaceuticals.

12 Claims, No Drawings

PROCESS FOR THE PREPARATION OF AROMATIC THIOCARBOXYLIC ACID AMIDES

The present invention provides a process for the preparation of aromatic thiocarboxylic acid amides.

Various methods for preparing thiocarboxylic acid amides are already known, the common characteristic of which is the following: other functional groups such as the nitrile, amide or amino group are converted to the thiocarboxylic acid amide group, or the latter group is incorporated into hydrocarbons via the reaction with N,N-disubstituted thiocarbamide acid chlorides in the presence of $AlCl_3$ or $SnCl_4$ (see Angew. Chemie 78 (1966), p. 517 sqq.; Synthesis 1972, 3, p. 101 sqq; B 101, 3 (1968), p. 3523; Patent of German Democratic Republic No. 61,799).

It has now been found that aromatic hydrocarbons optionally being substituted and having at least one hydrogen atom linked to an aromatic nucleus may be converted in one single operation to aromatic thiocarboxylic acid amides being unsubstituted at the nitrogen atom by using thiocyanates easily obtainable under industrial conditions or hydrogen thiocyanate in hydrofluoric acid.

The present invention therefore provides a process for the preparation of aromatic thiocarboxylic acid amides of the formula I

where Ar is an aromatic hydrocarbon radical, a diphenylene oxide or diphenylene sulfide radical, the radicals optionally containing also from 1 to 5, preferably from 1 to 3 identical or different substituents of the following kinds: alkyl, cycloalkyl, alkylene, alkoxy, alkylthio groups each having from 1 to 18 (preferably from 1 to 12, especially from 1 to 4) carbon atoms; hydroxy, phenyl, phenoxy, phenylthio groups; furthermore groups of the formulae $-O(CH_2)_n-COR$ or $-O-CH(CH_3)-COR$, n being 1 or 2, R being OH; OMe, Me being alkali metal; $OR^1$, $R^1$ being $C_1 - C_4$ alkyl; or

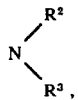

$R^2$ being H, $C_1 - C_4$ alkyl or phenyl, $R^3$ being H or $C_1 - C_4$ alkyl; the alkyl, cycloalkyl, alkylene, alkoxy and alkylthio groups for their part optionally being substituted by aliphatic, cycloaliphatic or aromatic radicals, and the alkylene groups optionally being connecting links of several, especially two, aromatic ring systems, and the total number of the aromatically linked carbon atoms being a maximum of 18, that of the non-aromatically linked carbon atoms being a maximum of 20; which process comprises reacting an aromatic hydrocarbon of the formula II $$Ar - H \qquad (II)$$

where Ar is as defined above, with hydrogen thiocyanate or a salt of thiocyanic acid in at least 90 weight % hydrofluoric acid.

The reaction is advantageously carried out as follows: first, a salt of thiocyanic acid in a form as finely distributed as possible is introduced, with thorough agitation and at a temperature of below 0° C, preferably down to −70° C, especially at −10° to −30° C, into the hydrofluoric acid or the solution or suspension of the aromatic hydrocarbon of formula II in hydrofluoric acid, or hydrogen thiocyanate is fed in. The reaction heat formed is optionally absorbed by additional cooling. In the first case, the aromatic hydrocarbon is added at the same or elevated temperature which may be at most the desired reaction temperature, preferably at a temperature of up to 20° C. Subsequently, the reaction mixture is heated to the reaction temperature of from about 0° to 120° C, preferably from 5 to 50° C, especially from 15° to 20° C, optionally under elevated pressure. The reaction is thus started, and it is completed with continuous agitation. A reaction without pressure at the boiling temperature of the hydrofluoric acid (about 19° C) is preferred.

It is likely that the reaction of thiocyanate or thiocyanic acid with the hydrofluoric acid yields thiocarbamide acid fluoride as intermediate product, which, in the temperature range of from 0° to 120° C, reacts subsequently with the aromatic hydrocarbon of formula II to yield thiocarboxylic acid amide. Possibly, the cation of the hydrogen thiocyanate reacts with the hydrofluoric acid to form a fluoride. The two-step reaction proceeds probably according to the following scheme, where Me is a cation or hydrogen:

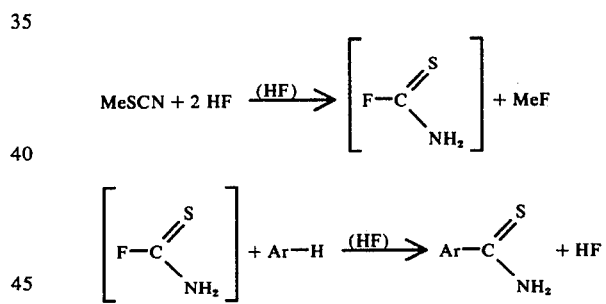

The formation of thiocarboxylic acid amide by reaction of the aromatic hydrocarbon of formula II occurs with substitution of a hydrogen atom at an aromatically linked carbon atom.

A special advantage of the process of the invention resides in the fact that it may be carried out in one single operation, and that neither a Lewis acid must be used nor the thiocarbamide acid fluoride prepared separately, since the latter one, after its formation, does not react according to the invention with the aromatic hydrocarbon of formula II at temperatures of below about 0° C, especially below −10° C. The reaction with the aromatic hydrocarbon in the hydrofluoric acid starts only in the temperature range of from 0° to 120° C and proceeds then substantially completely and with high yields within a reaction time ranging from a few hours to several days. The reaction speed generally increases with rising temperature.

The hydrofluoric acid serving as reaction medium and as reactant should contain at least 90 weight %, preferably at least 95 weight %, and especially from 98 to 100 weight % of hydrogen fluoride, the remainder optionally being water, and it is used in amounts of from about 2 to 50, preferably 4 to 10 parts by weight of hydrofluoric acid per part by weight of aromatic component of formula II employed. Since there is no formation of water in the reaction, most of the hydrofluoric acid used, apart from the portion possibly being converted to fluoride, may be recovered and reused after complete reaction.

As thiocyanate component, thiocyanic acid or the salts thereof are employed, especially the inorganic salts or the salts with onium bases, for example ammonium thiocyanate. Metal thiocyanates are preferred, especially alkali metal and alkaline earth metal thiocyanates, for example sodium, potassium, lithium, magnesium, calcium or barium thiocyanate. Sodium and potassium thiocyanate are preferred above all. The thiocyanates may be used per se or in combination with each other or with thiocyanic acid.

Suitable aromatic starting substances of formula II are simple aromatic hydrocarbons such as benzene, as well as condensed higher aromatic hydrocarbons, for example naphthalene, anthracene, phenanthrene, optionally having from 1 to 5, preferably from 1 to 3 identical or different substituents which generally contain a hydrogen atom linked to an aromatic nucleus. The substituted aromatic hydrocarbons of formula II contain as substitutents preferably groups which are inert under the process conditions of the invention. Suitable substituents are therefore especially the following: alkyl, cycloalkyl, alkylene, alkoxy or alkylthio groups each having from 1 to 18 carbon atoms, preferably 1 to 12, especially 1 to 4 carbon atoms; hydroxy, phenyl, phenyloxy, phenylthio groups of the formulae $-O(CH_2)_n-COR$ and $-OCH(CH_3)-COR$, where n is 1 or 2 and R is OH; OMe(Me is alkali metal, especially Na or K), $OR^1$ ($R^1$ is alkyl having from 1 to 4 carbon atoms) or

($R^2$ is H, alkyl having from 1 to 4 carbon atoms or phenyl; $R^3$ is H or alkyl having from 1 to 4 carbon atoms). The total number of the non-aromatically linked carbon atoms in the aromatic hydrocarbon of formula II should not be superior to 18 and that of the aromatically linked carbon atoms should not exceed 20. Besides alkylene groups, oxygen or sulfur atoms may form connecting links between aromatic ring systems, oxygen and sulfur optionally being at the same time elements of a heterocyclic ring, for example in diphenylene oxide or diphenylene sulfide.

Suitable aromatic starting compounds of formula II in accordance with the invention are for example: benzene, naphthalene, anthracene, phenanthrene, pyrene, chrysene, perylene. Preferred aromatic starting substances are the derivatives of benzene and naphthalene, for example toluene, xylene, trimethylbenzene, tetramethylbenzene, pentamethylbenzene, ethylbenzene, cumene, diisopropylbenzene, tetraline, hydrindene, naphthalene, methylnaphthalene, isopropylnaphthalene, di- or triisopropylnaphthalene, isododecylnaphthalene, octadecylnaphthalene, acenaphthene, fluorene, diphenylmethane, diphenyl ether, diphenyl sulfide, diphenylene oxide, diphenylene sulfide, phenol, butylphenol, dibutylphenol, nonylphenol, octadecylphenol, resorcinol, pyrocatechol, hydroquinone, α- and β-naphthol, the different cresols, xylenols and the mono- or dialkyl ethers thereof such as anisol, phenetol; α- and β-methoxynaphthalene, dimethoxynaphthalene and the corresponding thio-ethers such as thioanisol, thionaphtholmethyl, -ethyl, -butyl ether, phenoxyacetic acid, phenoxypropionic acid, α-methylphenoxyacetic acid, 2-, 3- and 4-methylphenoxyacetic acid, phenoxyacetic acid amide, phenoxyacetic acid anilide, β-naphthoxyacetic acid, β-naphthoxyacetic acid methyl ester, β-naphthoxyacetic acid dimethylamide, β-naphthoxyacetic acid anilide etc.

The two reactants, the thiocyanate or hydrogen thiocyanate on the one hand and the aromatic hydrocarbon of formula II on the other may be used in stoichiometric amounts; however, it may be useful to employ one of the two reactants in excess of, for example up to 50 mol%, preferably of from 5 to 20 mol%, if this seems to be advantageous for reasons of cost for one of the two starting components or because of an easier work-up of the reaction mixture. Higher excesses of the one or the other starting component may be used in principle, but do not bring about a further advantage.

In a preferred embodiment, the process of the invention may be carried out for example as follows: The thiocyanate and the aromatic hydrocarbon of formula II are introduced, at temperatures of from −70° to 0° C, preferably from −30° to −10° C, and with thorough agitation and intense cooling, into the hydrofluoric acid, and the mixture is subsequently maintained, with agitation, at a reaction temperature of from 0° C to the boiling point of the hydrofluoric acid. Advantageously, the reaction proceeds without pressure at boiling temperature of the hydrofluoric acid. Depending on the reactivity of the aromatic component of formula II, the reaction is complete within a few hours or proceeds for several days. However, the reaction may be accelerated and the reaction time reduced by using a suitable pressure vessel (for example a steel autoclave) and elevating the temperature up to 120° C, preferably up to 50° C. Advantageously, the temperature is raised slowly or step by step in intervals. The resulting aromatic thiocarboxylic acid amide of formula I obtained is obviously less unstable under the conditions of elevated reaction temperatures than the thiocarbamide acid fluoride probably formed as intermediate product.

After complete reaction, work-up of the reaction mixture is carried out for example by first distilling off substantially the hydrofluoric acid, subsequently stirring the residue with water, advantageously with icewater; or by stirring the whole reaction mixture including the hydrofluoric acid with icewater, and separating then the precipitated aromatic thiocarboxylic acid amide.

The fluorides, for example alkali metal, alkaline earth metal or ammonium fluoride, formed possibly in the reaction, may be eliminated by washing with water as far as they are water-soluble. In the case of sparingly soluble fluorides, they may be eliminated by dissolving the aromatic thiocarboxylic acid amide formed in an inert organic solvent, for example toluene, chlorobenzene, diethyl ether, ethyl acetate or butyl acetate, separating it from undissolved fluoride and isolating it from the solution.

When the reaction mixture is worked up by introducing the crude product into water, the aromatic thiocarboxylic acid amide of formula I generally precipitates in crystallized form or separates in oily or pasty form and may be purified according to known methods, for example by recrystallization from inert organic solvents, or in the case of phenolic thiocarboxylic acid amides by dissolution in an aqueous alkaline solution and subsequent precipitation caused by acidifying the solution.

The aromatic thiocarboxylic acid amides prepared according to the invention, which are substances known from the literature, are obtained with high purity degrees. They are interesting preliminary products for the preparation of nitriles amides, carboxylic acids, heterocyclic compounds, or for the manufacture of plant protection products and pharmaceuticals.

The following examples illustrate the invention.

EXAMPLE 1

In a polyethylene vessel having a capacity of 1 liter, at −20° C and with agitation, 46 g of ammonium thiocyanate (0.6 mol) and subsequently 53 g of ethylbenzene (0.5 mol) are added in portions to 0.5 l of 98% hydrofluoric acid. Subsequently, agitation is continued for 20 hours at room temperature, and the reaction mixture is then poured onto ice, thus causing the separation of a precipitate which slowly crystallizes. The precipitate is suction-filtered and washed with water. By steam distillation, about 10 g of ethylbenzene are recovered from the precipitate. After drying, 66 g (0.4 mol) of ethyl-thiobenzamide having a slightly yellow color and a melting point of 115 − 117° C are obtained, which corresponds to a conversion rate of 80% relative to the ethylbenzene used. The yield, relative to converted ethylbenzene, is 95% of the thoeretical yield. The product can be recrystallized from toluene or chlorobenzene. The gas chromatogram shows that substitution by the thioamide group has occured in p-position at a rate of more than 95%. The 4-ethylbenzonitrile may be obtained from the thioamide in known manner using alkali, thereby splitting off $H_2S$.

EXAMPLE 2

2,4,6-trimethyl-thiobenzamide

When 40 g of ammonium thiocyanate (0.53 mol) in 0.3 l of 98% hydrofluoric acid are reacted as described in Example 1 with 60 g of mesitylene (0.5 mol), 90 g of 2,4,6-trimethylthiobenzamide having a melting point of 198 − 200° C are obtained, which corresponds to a quantitative yield relative to mesitylene. A sample recrystallized from xylene or water has a melting point of 208 − 210° C. By alkaline splitting-off of $H_2S$, the known cyanomesitylene is obtained from the product.

EXAMPLE 3

α-thionaphthoic acid amide

At a temperature and in the manner as described in Example 1, 39 g of potassium thiocyanate (0.4 mol) are introduced into 0.3 l of 98% hydrofluoric acid, 42 g of naphthalene (0.33 mol) are added and the mixture is agitated for 2 days at room temperature. After work-up, 54 g of crude α-thionaphthoic acid amide (0.32 mol) having a melting point of 119° C are obtained. A sample recrystallized from xylene has a melting point of 122° − 125° C. By alkaline splitting of the product, pure α-naphthonitrile may be obtained.

EXAMPLE 4

4-ethylthiobenzamide

At a temperature of below −10° C, the same starting components and amounts as indicated in Example 1 are stirred, subsequently introduced into a shaking autoclave made of steel, the internal temperature of which is maintained at 20° C for 3 hours, at 40° − 50° C for another 3 hours, at 70° − 80° C for another 3 hours and at 100° − 110° C for a final 3 hours. Subsequently, the reaction mixture is cooled to a temperature of below 20° C, stirred with ice, the precipitate obtained is suction-filtered and the 4-ethyl-thiobenzamide is obtained with about the same yield as indicated in Example 1.

EXAMPLE 5

1-methyl-4-thionaphthoic acid amide

At a temperature and in the manner as described in Example 1, 39 g of potassium thiocyanate (0.4 mol) are stirred into 0.3 l of 98% hydrofluoric acid, 47 g of α-methylnaphthalene (0.33 mol) are added, and the mixture is stirred for 4 hours at room temperature. The reaction is then complete. Work-up is possible by stirring with ice, as described in the preceding Examples, or by distilling off the greater part of the hydrofluoric acid in a steel apparatus before stirring with ice. 64 g of 1-methyl-4-thionaphthamide having a melting point of 143° − 145° C are obtained, which corresponds to a yield of 97% of the theoretical yield, relative to α-methyl-naphthalene used.

EXAMPLE 6

4-hydroxytoluene-3-thiocarboxylic acid amide

According to Example 5, 39 g of potassium thiocyanate (0.4 mol) are stirred with 0.3 l of 98% hydrofluoric acid, and 35 g of p-cresol (0.32 mol) are added. After a reaction time of 24 hours at room temperature, 80% of the cresol are converted to 4-hydroxytoluene-3-thiocarboxylic acid amide having a melting point of 129° − 130° C. The NMR spectrum and the conversion to nitrile prove the substitution by the thioamide group in 3-position.

EXAMPLE 7

4-hydroxy-thiobenzoic acid amide

At a temperature and in the manner as described in Example 1, 69 g of potassium thiocyanate (0.7 mol) and 52 g of phenol (0.55 mol) are stirred with 0.5 l of 98% hydrofluoric acid, and subsequently, the mixture is stirred for 3 days at room temperature. 0.3 l of hydrofluoric acid are then distilled off at normal pressure and a bath temperature of up to 60° C, the remainder is cooled and the residue is stirred with ice and water. The crude product precipitated is suction-filtered and may be purified by dissolving in dilute soda solution at room temperature, clarifying the solution and subsequent precipitation of the product with mineral acid or by recrystallization from water. The 4-hydroxy-thiobenzamide so obtained has a melting point of 192° − 193° C. The yield is 85% of the theoretical yield, relative to the phenol used.

EXAMPLE 8

2-hydroxyanisol-thiocarboxylic acid amide

At a temperature and in the manner as described in Example 1, 39 g of potassium thiocyanate (0.4 mol)

and 43.4 g of guaiacol (0.35 mol) are stirred with 0.3 l of 98% hydrofluoric acid, and the mixture is then stirred for 8 hours at room temperature. Subsequently, it is poured onto ice, decanted from the crude reaction product precipitated in oily form, and this crude product is stirred with 10% sodium hydroxide solution until a pH of 8 is attained. The sodium salt of the reaction product which has precipitated in crystallized form is suction-filtered, stirred with water, acidified and the precipitate so obtained is again suction-filtered. The 2-hydroxyanisol-thiocarboxylic acid amide obtained with a 70% yield relative to the guaiacol used has a melting point of 70° – 71° C.

EXAMPLE 9

2,4-dihydroxy-thiobenzamide

At a temperature and in the manner as described in Example 1, 39 g of potassium thiocyanate (0.4 mol) and 38.5 g of resorcinol (0.35 mol) are stirred with 0.3 l of 98% hydrofluoric acid, and subsequently, the mixture is stirred for 5 hours at room temperature. 0.25 l of hydrofluoric acid are then distilled off, and the residue is mixed with a small amount of ice, which causes 47 g of 2,4-dihydroxy-thiobenzamide to crystallize. This corresponds to a yield of 80% of the theoretical yield, relative to the resorcinol used. The melting point is 164° – 166° C.

EXAMPLE 10

2,4-dimethoxy-thiobenzamide

At a temperature as indicated in Example 1, 39 g of potassium thiocyanate (0.4 mol) and 48.3 of resorcinoldimethyl ether (0.35 mol) are stirred with 0.35 l of 95% hydrofluoric acid, the mixture is then stirred for 6 hours at room temperature and then poured onto ice and worked up. With a practically quantitative yield, crude 2,4-dimethoxy-thiobenzamide having a melting point of 115° – 118° C is obtained. It is dissolved then in methanol, clarified and precipitated with water. The product so purified has a melting point of 136° – 138° C.

EXAMPLE 11

2,8-dihydroxy-thionaphthoic acid amide

At a temperature as indicated in Example 1, 39 g of potassium thio-cyanate (0.4 mol) and 53 g of 1,7-dihydroxynaphthalene (0.33 mol) are stirred with 0.3 l of 98% hydrofluoric acid, and the mixture is then stirred for 10 hours at room temperature. Subsequently, the batch is poured into icewater and stirred until the reaction product has dissolved for its greater part. The solution is then clarified, salted out with potassium chloride, the 2,8-dihydroxy-thionaphthoic acid amide precipitated is suction-filtered, washed with acetone and dried. Yield: 95% of the theoretical yield, relative to 1,7-dihydroxy-naphthalene used. The product decomposes at about 195° C.

EXAMPLE 12

3,4-dimethyl-thiobenzamide

At a temperature as indicated in Example 1, 59 g of potassium thiocyanate (0.6 mol) and 79.5 g of o-xylene (0.75 mol) are stirred with 0.5 l of 98% hydrofluoric acid. and the mixture is then stirred for 10 hours at room temperature. Subsequently, the batch is poured onto ice, the precipitated product is suction-filtered after having been stirred for one-half hour, and the greater part of the non-reacted o-xylene (15 g) is separated from the still moist filter cake by steam distillation. The distillation residue is subsequently suction-filtered and dried. The yield of dimethylthiobenzamide having a melting point of 120° – 125° C is 99 g and therefore quantitative, relative to the potassium thiocyanate used.

EXAMPLE 13

2,7-dimethyl-1-thionaphthamide

At a temperature and in the manner as indicated in Example 1, 39 g of potassium thiocyanate (0.4 mol) and 52 g of 2,7-dimethylnaphthalene (0.33 mol) are stirred with 300 ml of 98% hydrofluoric acid, the mixture is then stirred for 10 hours at room temperature, and the bath is worked up by mixing with ice as described in Example 1. 72 g of dimethylthionaphthamide having a melting point of 138° – 141° C are obtained, which corresponds to a quantitative yield relative to 2,7-dimethylnaphthalene used. The product recrystallized from chlorobenzene has a melting point of 157° – 159° C.

EXAMPLE 14

Isododecyl-thionaphthoic acid amide

At a temperature of below −10° C, 29.4 g of potassium thiocyanate (0.3 mol) and subsequently, at room temperature, 74 g of isododecylnaphthalene, ind. grade (0.33 mol), are introduced into 0.3 ml of 98% hydrofluoric acid. After agitation at room temperature for 24 hours, the batch is mixed with ice, the reaction product absorbed in ethyl acetate, dried over sodium sulfate and the ethyl acetate is distilled off. The non-reacted isododecyl-naphthalene is separated from the sirupy reaction product by extraction with petroleum ether. The isododecyl-thionaphthoic acid amide is obtained with an about 80% yield, relative to the isododecyl-naphthalene used.

EXAMPLE 15

4-methyl-thioanisol-2-thiocarboxylic acid amide

At a temperature and in the manner as indicated in Example 1, 39 g of potassium thiocyanate (0.4 mol) and 46 g of 4-methyl-thioanisol (0.33 mol) are stirred with 0.3 l of 98% hydrofluoric acid. The mixture is then stirred first for 10 hours at room temperature and then for 3 hours in a steel autoclave at 40° – 50° C, subsequently cooled, the reaction mixture is poured onto ice, the 4-methyl-thioanisol-2-thiocarboxylic acid amide precipitated is suction-filtered and dried. The yield (54 g) is 81% of the theoretical yield, relative to the 4-methyl-thioanisol used. After recrystallization of the product from chlorobenzene, the melting point is 160° C.

EXAMPLES 16 – 32

In the following Examples 16 to 32, 39 g of potassium thiocyanate (0.4 mol) each are stirred with 0.3 l of 98% hydrofluoric acid at a temperature of below −10° C, subsequently 0.33 mol each of the cited aromatic compound is added, and the mixture obtained is stirred subsequently for 24 hours at room temperature. The batch is then poured onto ice and the reaction product isolated.

In the following Table I, there are listed the aromatic compounds used as starting material, the thiocarboxylic acid amide derivatives thereof, the conversion rate relative to the aromatic compound used, the yield relative to the reacted amount of aromatic compound and the melting point of the crude thiocarboxylic acid amide obtained.

methanol, gives 100 g of phenoxyacetic acid methyl ester-4-thiocarboxylic acid amide having a melting point of 148° C, corresponding to a yield of 83.5% of the theoretical yield.

EXAMPLE 35

Phenoxypropionic acid 4-thiocarboxylic acid amide

TABLE I

| Example | Starting material | Reaction product | Conversion rate in % | Yield in % rel. to the conversion | Melting point ° C of the reaction product |
|---|---|---|---|---|---|
| 16 | toluene | 80 % 4-methylthiobenzamide<br>20 % 2-methylthiobenzamide | 60 | 98 | 168 |
| 17 | m-xylene | 2,4-dimethylthiobenzamide | 90 | 100 | 74 – 76 |
| 18 | cumene | 4-isopropylthiobenzamide | 45 | 97 | 142 – 144 |
| 19 | 1,2,4-trimethyl benzene | 2,4,5-trimethylthiobenzamide | 100 | 100 | 118 – 120 |
| 20 | acenaphthene | acenaphthene-5-thiocarboxylic acid amide | 86 | 95 | 184 |
| 21 | anthracene | anthracene-x-thiocarboxylic acid amide | 55 | 95 | 179 – 183 |
| 22 | fluorene | fluorene-x-thiocarboxylic acid amide | 60 | 98 | 219 |
| 23 | pyrene | pyrene-x-thiocarboxylic acid amide | 60 | 100 | 115 – 121 |
| 24 | phenanthrene | phenanthrene-x-thiocarboxylic acid amide | 15 | 95 | 112 – 115 |
| 25 | tetralin | abt. 50 % α-tetralin-thiocarboxylic acid amide<br>abt. 50 % β-tetralin-thiocarboxylic acid amide | 98 | 100 | 153 – 154 |
| 26 | β-naphthol | 2-hydroxy-1-thionaphthoic acid | 60 | 92 | 145 – 147 |
| 27 | hydroquinone monomethyl ether | 4-hydroxyanisol-x-thiocarboxylic acid amide | 60 | 98 | 149 |
| 28 | hydroquinone diethyl ether | 2.5-diethoxy-thiobenzamide | 95 | 100 | 160 – 162 |
| 29 | anisol | 4-methoxy-thiobenzamide | 98 | 100 | 139 – 142 |
| 30 | 3,5-di-tert.-butyl-toluene | 6-methyl-2,4-di-tert.-butyl-thiobenzamide | 96 | 100 | 167 – 169 |
| 31 | pentamethyl-benzene | pentamethylthiobenzamide | 100 | 100 | 190 – 192 |
| 32 | veratrol | 3.4-dimethoxy-thiobenzamide | 100 | 100 | 184 – 186 |

EXAMPLE 33

Phenoxycarboxylic acid-4-thiocarboxylic acid amide

In a polyethylene vessel having a capacity of 1 liter, 54 g of sodium thiocyanate (0.66 mol) and subsequently 83 g of phenoxyacetic acid (0.55 mol) are introduced in portions and with agitation into 0.5 l of 98% hydrofluoric acid at a temperature of −20° C. Agitation is continued for 3 days at room temperature, the greater part of the hydrofluoric acid is then distilled off, and the residue is stirred with ice. After suction-filtration and drying, 112 g of phenoxyacetic acid-4-thiocarboxylic acid amide having a melting point of 211° C are obtained, which corresponds to a yield of 96.5% of the theoretical yield, relative to the phenoxyacetic acid used.

EXAMPLE 34

Phenoxyacetic acid methyl ester-4-thiocarboxylic acid amide

When, in analogy to Example 33, 65 g of potassium thiocyanate (0.66 mol) in 0.5 l of 98% hydrofluoric acid are reacted with 84 g of phenoxyacetic acid methyl ester (0.50 mol), a crude product is obtained which, after dissolution and precipitation in 500 ml of As described in Example 33, 39 g of potassium thiocyanate (0.4 mol) and 55 g of phenoxypropionic acid (0.33 mol) are stirred at the temperature indicated in Example 33 with 0.3 l of 98% hydrofluoric acid. After 2 days at room temperature, the mixture is stirred with ice, the reaction product is suction-filtered and dried. 53 g of phenoxypropionic acid-4-thiocarboxylic acid amide having a melting point of 193° C are obtained, which corresponds to a yield of 71% of the theoretical yield, relative to the phenoxypropionic acid used.

EXAMPLES 36 to 41

In the following Examples 36 to 41, 30 g each of potassium thiocyanate (0.3 mol) are stirred with 0.3 l of 98% hydrofluoric acid at a temperature of below −10° C, subsequently, 0.25 mol each of the cited aromatic compound is added, and the mixture so obtained is stirred at room temperature for 24 hours. Subsequently, the batch is poured onto ice and the reaction product is isolated.

In the following Table II, there are listed the aromatic compounds used as starting material, the thiocarboxylic acid derivatives thereof, the yield relative to the aromatic compound used and the melting point of the crude thiocarboxylic acid amide obtained. The symbol X in column 3 represents isomer mixtures formed.

TABLE II

| Example | Starting material | Reaction product | Yield % | Melting point (°C) |
|---|---|---|---|---|
| 36 | phenoxyacetic acid amide | -4-thiocarboxylic acid amide | 77 | 222 |
| 37 | 1-naphtoxy-acetic acid | -4-thiocarboxylic acid amide | 91 | 194 |
| 38 | 2-methyl-phenoxyacetic acid | -X-thiocarboxylic acid amide | 95 | 212 |
| 39 | 3-methyl-phenoxyacetic acid | -X-thiocarboxylic acid amide | 90 | 202 |
| 40 | 4-methyl-phenoxyacetic acid | -2-thiocarboxylic acid amide | 98 | 185 |
| 41 | 2,5-dimethyl-phenoxyacetic acid | -4-thiocarboxylic acid amide | 94 | 151 |
| 42 | phenoxyacetic acid anilide | -4-thiocarboxylic acid amide | 80 | 205 |

I claim:

1. A process for the preparation of an aromatic thiocarboxylic acid amide having the formula

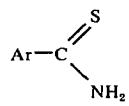     (I)

wherein Ar is an unsubstituted aromatic hydrocarbon, or an aromatic hydrocarbon substituted by substituent groups which are substantially inert under the process conditions, said process comprising reacting a compound of the formula

     (II), wherein Ar is as defined above, with hydrogen thiocyanate, or an inorganic metal salt or ammonium salt of thiocyanic acid and carrying out the reaction in at least 90 weight percent hydrofluoric acid, wherein the hydrogen thiocyanate or said salt of thiocyanic acid is added to the hydrofluoric acid at a temperature of about −70° to 0° C, the aromatic hydrocarbon compound II is added and the reaction mixture temperature is subsequently gradually increased to a temperature of from about 0° to 120° C.

2. The process of claim 1, which comprises using from 2 to 50 parts by weight of hydrofluoric acid per part by weight of aromatic hydrocarbon of formula II.

3. The process of claim 1, wherein the hydrofluoric acid contains at least 95 weight % of hydrogen fluoride.

4. The process of claim 1, which comprises using the thiocyanate or the hydrogen thiocyanate on the one hand and the aromatic hydrocarbon of formula II on the other in about stoichiometric amounts, or using one of the reactants in an excess of up to 50 mol %.

5. The process of claim 1, which comprises using sodium or potassium thiocyanate.

6. The process of claim 1 wherein the salt of thiocyanic acid is a member selected from the group consisting of ammonium and alkali metal salts of thiocyanic acid.

7. The process of claim 1 wherein the salt of thiocyanic acid is a member selected from the group consisting of alkaline earth metal salts of thiocyanic acid.

8. The process of claim 1 wherein the hydrogen thiocyanate or salt of thiocyanic acid is added to the hydrofluoric acid at a temperature of about −10° to −30° C and the aromatic compound is added at a temperature of −10° to −30° C and the reaction mixture is subsequently heated to a temperature of 15° to 20° C.

9. The process of claim 1 wherein the hydrogen thiocyanate or salt of thiocyanic acid is added to the hydrofluoric acid at a temperature of about −10° to −30° C and the aromatic compound is added at a temperature of about 15° to 20° C.

10. The process of claim 1 wherein Ar is a member selected from the group consisting of benzene and benzene substituted by a member of the group consisting of ethyl, tri-methyl, methyl and hydroxy, hydroxy, hydroxy and methoxy, di-hydroxy, di-methoxy, di-methyl, methyl and mercaptomethyl, isopropyl, diethoxy, methoxy, di-tertiary butyl and methyl, pentamethyl, —OCH$_2$COOH, —OCH$_2$COOCH$_3$, —OCH$_2$CH$_2$COOH, —OCH$_2$CONH$_2$, methyl and —OCH$_2$COOH, dimethyl and —OCH$_2$COOH, and —OCH$_2$CONH CC$_6$H$_5$ 11. The process of claim 1 wherein Ar is a member selected from the group consisting of naphthalene and naphthalene substituted by a member of the group consisting of methyl, di - hydroxy, di - methyl, isododecyl, hydroxy, and —OCH$_2$COOH—.

12. A process for the preparation of an aromatic thiocarboxylic acid amide having the formula

     (I)

wherein Ar is unsubstituted or substituted by substituent groups which are substantially inert under the process conditions and is a member selected from the group consisting of benzene, naphthalene, tetraline, acenaphthene, anthracene, fluorene, pyrene and phenanthrene; and benzene substituted by a member of the group consisting of ethyl, tri-methyl, methyl and hydroxy, hydroxy, hydroxy and methoxy, di-hydroxy, di-methoxy, di-methyl, methyl and mercaptomethyl, isopropyl, di-ethoxy, methoxy, di-tertiary butyl and methyl, pentamethyl, —OCH$_2$COOH, —OCH$_2$COOCH$_3$, —OCH$_2$CH$_2$COOH, —OCH$_2$CONH$_2$, methyl and —OCH$_2$COOH, dimethyl and —OCH$_2$COOH, and —OCH$_2$CONH(C$_6$H$_5$); and naphthalene substituted by a member of the group consisting of di-hydroxy, di-methyl, isododecyl, hydroxy, and —OCH$_2$COOH.

which process comprises reacting a compound of the formula

Ar–H    (II), wherein Ar is as defined above, with hydrogen thiocyanate, or an inorganic metal salt of thiocyanic acid and carrying out the reaction in at least 90 weight percent hydrofluoric acid, wherein the hydrogen thiocyanate or said salt of thiocyanic acid is added to the hydrofluoric acid at a temperature of about −70° to 0° C the aromatic hydrocarbon compound II is added and the reaction mixture temperature is subsequently gradually increased to a temperature of from about 0° to about 120° C.

* * * * *